United States Patent [19]

Szegö et al.

[11] 4,329,338

[45] May 11, 1982

[54] COMPOSITIONS FOR USE AS COSMETICS

[75] Inventors: Ferenc Szegö; Antal Makk, both of Budapest, Hungary

[73] Assignee: Ferrokemia Ipari Szovetkezet, Budapest, Hungary

[21] Appl. No.: 114,425

[22] Filed: Jan. 22, 1980

[30] Foreign Application Priority Data

Jun. 1, 1979 [HU] Hungary .................. FE 1046

[51] Int. Cl.³ .................. A61K 31/70; A61K 31/455; C07H 13/10
[52] U.S. Cl. .................. 424/180; 424/55; 424/57; 424/70; 424/266; 424/358; 424/365; 536/18.7; 536/115; 536/119; 536/120; 536/55
[58] Field of Search .................. 424/180, 266; 536/4, 536/115, 119

[56] References Cited

U.S. PATENT DOCUMENTS

| 3,950,324 | 4/1976 | Gey et al. | 536/4 |
| 4,017,502 | 4/1977 | Letelier et al. | 424/266 |
| 4,112,075 | 9/1978 | Baschang et al. | 536/4 |
| 4,201,235 | 5/1980 | Ciavatta | 424/266 |

OTHER PUBLICATIONS

Brox et al., "Chem. Abst.", vol. 68, 1968, p. 11618(a).
Rau, "Chem. Abst.", vol. 75, 1971, p. 25432.

Primary Examiner—Johnnie R. Brown
Attorney, Agent, or Firm—Young & Thompson

[57] ABSTRACT

The invention relates to new compositions to be used as cosmetics. The new cosmetics according to the invention contain as active agent 0.06 to 10% by weight of a reaction product of nicotinic acid, a nicotinic acid salt or a nicotinic acid halide and a polyhydroxy compound of the general formula (I),

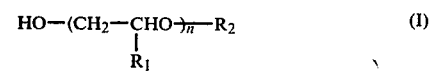

wherein
n is an integer of 1 to 15 and $R_1$ and $R_2$ each stand for hydrogen, or $R_2$ represents hydrogen and $R_1$ is an alkyl group, or $R_1$ is hydroxyalkyl and $R_2$ is an alkyl group, or when n is equal to 1, $R_1$ and $R_2$ may also form together a group of the general formula $—(CHOH)_m—$, wherein m is an integer of 1 to 4, or a group of the general formula $—(CHOH)_q—CHNH_2—(CHOH)_p—$, wherein Q is an integer of 0 to 2 and p is an integer of 1 to 3, or $R_1$ may represent a group of the general formula $—(CHOH)_m—H$, wherein m is an integer of 1 to 4, and at the same time $R_2$ stands for hydrogen.

These active agents are either physiologically active or potentiate the biological effects of other physiologically active substances. The active agents exert beneficial effects in cosmetics, such as in liniments for stimulating scalp or hair bulbs, liniments against rheumatism, hair shampoos, etc.

The active agents defined above are prepared by reacting a compound of the general formula (I) or a benzylidene derivative thereof with nicotinic acid, a nicotinic acid salt or a nicotinic acid halide.

11 Claims, No Drawings

COMPOSITIONS FOR USE AS COSMETICS

The invention relates to new compositions which can be used as cosmetics.

The cosmetics according to the invention include e.g. liniments for stimulating scalp and hair roots, hair shampoos, liniments against rheumatism, tooth pastes against paradentosis, etc.

It is known that nicotinic acid and certain derivatives thereof (such as papaverine nicotinate, ethanolamine nicotinate, etc.) exert vasodilating effects and act directly on the vasomotor centre.

The reaction products (e.g. esters or salts) of certain polyhydroxy compounds formed with nicotinic acid or nicotinic acid derivatives, applied as active ingredients in the compositions according to the invention, exert physiological effects per se or potentiate the effects of physiologically active substances, particularly of those present in liniments, ointments or tinctures. More particularly, the active ingredients of the new compositions promote circulation and provoke hyperaemia, thereby increasing or stimulating the effects of other physiologically active substances. Some representatives of the active agents exert beneficial physiological effects per se, i.e. even in the absence of other physiologically active substances. The active agents of the new compositions according to the invention have the advantage over the conventional nicotinic acid derivatives that the nicotinic acid moiety is linked to a non-toxic organic molecule which enables the compound to penetrate into the skin. Having entered the organism, the compound spontaneously decomposes partially or completely, and the resulting compounds (nicotinic acid and the organic polyhydroxy derivative) exert further physiological effects and participate in the biochemical processes of the organism.

It has been found that some representatives of the compounds built up from nicotinic acid and a component containing an oxygen atom in ether or lactone bond and several hydroxy groups (i.e. polyols containing optionally one or more oxygen atoms in ether or lactone bond and optionally an amino group as well) can be applied particularly well in liniments, cosmetics for skin treatment, etc. Of the polyhydroxy components sugars, sugar alcohols, deoxyamino sugars and polyglycols are particularly preferable. Furthermore, it has been found that the most preferred representatives of the nicotinic acid derivatives of the above polyfunctional compounds are those prepared by reacting one mole of a polyhydroxy compound with only one mole of nicotinic acid or nicotinic acid derivative, although the polyhydroxy compounds, owing to their polyfunctional nature, are capable of reacting with more than one molecule of nicotinic acid or nicotinic acid derivative.

Thus, in accordance with the invention, nicotinic acid esters or nicotinic acid salts of the above polyhydroxy compounds are prepared, and these substances are applied as active agents in various cosmetics. Of the sugar esters the monoester wherein the glycosidic hydroxy group is acylated with nicotinic acid is particularly preferable.

According to one aspect of the invention nicotinic acid derivatives of the above polyhydroxy compounds are prepared in stable form easy to handle. Some of the compounds prepared according to the invention are known, whereas other representatives have not been described in the literature so far.

The process of the invention is performed so that a compound of the general formula (I),

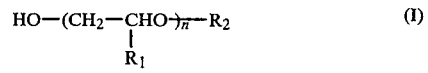

$$HO-(CH_2-CHO)_n-R_2 \qquad (I)$$
$$\phantom{HO-(CH_2-C}|$$
$$\phantom{HO-(CH_2-CH}R_1$$

wherein
n is an integer of 1 to 15 and $R_1$ and $R_2$ each stand for hydrogen, or $R_2$ represents hydrogen and $R_1$ is an alkyl group, or
$R_1$ is hydroxyalkyl and $R_2$ is an alkyl group, or
when n is equal to 1, $R_1$ and $R_2$ may also form together a group of the general formula —(-CHOH)$_m$—, wherein m is an integer of 1 to 4, or a group of the general formula —(CHOH)$_q$—CHNH$_2$—(CHOH)$_p$—, wherein q is an integer of 0 to 2 and p is an integer of 1 to 3, or $R_1$ may represent a group of the general formula —(CHOH)$_m$—H, wherein m is an integer of 1 to 4, and at the same time $R_2$ stands for hydrogen,
or a benzylidene derivative thereof is reacted with nicotinic acid, a nicotinic acid salt or a nicotinic acid halide. The reaction is performed under heating, optionally in the presence of p-toluenesulfonic acid and/or sulfuric acid or sodium ethoxide. As reaction medium the reactant itself, an inert solvent or water can be used. It is preferred to use the reactant itself as reaction medium, since in this instance the compound need not be isolated from the reaction mixture when processing it into a composition. In this case substances other than nicotinic acid or a nicotinic acid derivative and the polyhydroxy compound, utilized in excess, are not used in the reaction in significant amounts. 1 mole of nicotinic acid is reacted with 1 to 10 moles of a compound having the general formula (I). In this instance the end-product is obtained as a solution in the excess of the reactant. Such solutions can be stored for a prolonged time and can be handled very easily when converting them into compositions. Aqueous solutions of the active agents prepared as described above can also be stabilized according to the invention. It has been observed that the active agents are stable in the presence of an excess of the starting polyhydroxy compound, and, in general, in the presence of polyhydroxy compounds (sugars, sugar alcohols, etc.) or in the form of more concentrated solutions, and the active agents hydrolyze into their components only in higher dilution or when the biological processes start.

The cosmetics according to the invention contain the active agents, prepared as described above, in an amount of 0.06 to 10%, together with other known active agents, auxiliary agents and/or additives (such as detergents, known plant extracts, drugs of plant origin, odouring substances, carbohydrates, vitamins, surfactants, solvents, ointment bases, etc.) selected in accordance with the field of use.

One type of the compositions according to the invention contains carbohydrates as additives. It has been found that the so-called affinate, a by-product formed in sugar plants during the affination step of the refining operation, contains biologically active substances which exert very favourable effects e.g. on the scalp.

Affinate has been considered so far as a worthless by-product, useful only as a fodder additive in animal husbandry. Affinate contains various carbohydrates, proteins, pectin, saponin, organic acids, calcium salts, vitamins and various other organic compounds with hitherto unknown structures. It has been found that compositions which contain the nicotinic acid derivatives prepared according to the invention together with known drugs of plant origin in the presence of affinate as carbohydrate exert an unexpectedly high biological effect. The biological effect is often faster than observed with the known compositions. Therefore the compositions according to the invention which contain a nicotinic acid derivative prepared as described above, a conventional drug of plant origin and affinate as carbohydrate are particularly preferred.

Generally no preservative is added to the composition according to the invention, but in this instance the composition is subjected to heat treatment in order to prepare a stable and storable product. In the heat treatment the mixture containing the active ingredient and the additives is maintained at 50° to 90° C. for 5 to 40 minutes.

The invention is elucidated in detail by the aid of the following non-limiting Examples.

EXAMPLE 1

18 g (0.1 moles) of D-glucose are dissolved in about 74 g of dioxane under gentle heating, and 7.08 g (0.05 moles) of nicotinoyl chloride are added to the solution. The solution is maintained at 70° to 80° C., and 4.2 g of sodium hydrocarbonate are added thereto. The reaction mixture is stirred at the same temperature until the evolution of carbon dioxide gas ceases. The reaction mixture is allowed to cool and carbon dioxide is allowed to leave the mixture. 100 g of a solution, containing about 14.3 g of dissolved d-glucose mononicotinate (equivalent to 6.0 g, i.e. 0.05 moles, of nicotinic acid), 9 g of dissolved d-glucose and about 3.0 g of sodium chloride, are obtained. The 74 g of dioxane forms the solvent of the solution.

EXAMPLE 2

18.2 g (0.1 moles) of mannitol or sorbitol are dissolved in 74.0 g of dioxane under gentle heating, and 7.08 g (0.05 moles) of nicotinoyl chloride are added to the solution. The mixture is heated to 70° to 80° C., 4.2 g of aniline are added, and the reaction is conducted at the same temperature for one hour. Thereafter the mixture is allowed to cool. 100 g of a solution, containing 14.3 g of dissolved mannitol or sorbitol mononicotinate (equivalent to 6.0 g, i.e. 0.05 moles, of nicotinic acid), and 9.1 g (0.05 moles) mannitol or sorbitol are obtained.

EXAMPLE 3

Preparation of a solution containing 2-deoxy-2-aminoglucose nicotinate (nicotinic acid salt of glucosamine)

10.7 g (0.05 moles) of glucosamine hydrochloride are dissolved in 52 ml of water. 6.3 g (0.051 moles) of nicotinic acid are suspended in 20 ml of water containing one drop of alcohol, and a solution of 2 g (0.05 moles) of sodium hydroxide in 10 ml of water is added dropwise to the suspension, whereupon nicotinic acid dissolves. The resulting solution is admixed with the aqueous solution of glucosamine hydrochloride. 100 g of a slightly yellowish solution are obtained, which contains 15 g of the nicotinic acid salt of glucosamine (equivalent to 6 g of nicotinic acid) and 3 g of sodium chloride. The optical rotation power of the resulting solution is $[\alpha]_D = +35.8°$.

EXAMPLE 4

Preparation of an ethyleneglycol solution of ethyleneglycol mononicotinic acid ester 6 g of nicotinic acid are added to 94 g of glycol, and the solids are dissolved by heating. The resulting solution is heated to 170° to 190° C., and 0.1 g of p-toluenesulfonic acid is added. The mixture is stirred at this temperature until its acid number decreases below 3. 100 g of a solution, containing 8.35% of ethyleneglycol mononicotinic acid ester (equivalent to 6% of nicotinic acid) are obtained.

EXAMPLE 5

6 g of nicotinic acid are added to 94 g of polyethylene glycol with an average molecular weight of 400. Thereafter one proceeds as described in Example 4. 100 g of a solution, containing about 25.2% of polyethylene glycol mononicotinic acid ester (equivalent to 6% of nicotinic acid), are obtained.

EXAMPLE 6

6 g of nicotinic acid are added to 94 g of dipropylene glycol. Thereafter one proceeds as described in Example 4. 100 g of a solution, containing about 12% of dipropylene glycol mononicotinic acid ester (equivalent to 6% of nicotinic acid), are obtained.

EXAMPLE 7

6 g of nicotinic acid are added to 94 g of propylene glycol. Thereafter one proceeds as described in Example 4. 100 g of a solution, containing about 9% of propylene glycol mononicotinic acid ester (equivalent to 6% of nicotinic acid), are obtained.

EXAMPLE 8

15.2 g (0.1 mole) of arabite are dissolved in 60.6 g of dioxane under gentle heating. 14.1 g (0.1 moles) of nicotinoyl chloride are added to the solution, the mixture is heated to 60° to 100° C., and 10 g of pyridine are introduced. The reaction is conducted at the same temperature for one hour, and then the mixture is allowed to cool. 100 g of a solution, containing about 25.7 g (0.1 mole) of arabite mononicotinic acid ester (equivalent to 12.3 g of nicotinic acid) are obtained.

EXAMPLE 9

Preparation of 1-O-nicotinoyl-4,6-O-benzylidene-$\beta$-D-glycopyranose 2.9 g of 4,6-O-benzylidene-D-glycopyranose sodium salt are suspended in 30 ml of dry dichloromethane, and 1.39 g (0.98 mmole) of nicotinoyl chloride are added. The mixture is shaken at room temperature for 9 hours and then evaporated to dryness in vacuo. The resulting solid substance is taken off in 10 ml of distilled water, the mixture is neutralized with sodium hydrocarbonate solution, and then maintained at 0° to −5° C. for one hour. The separated white crystals are filtered off by suction, washed with cold water and dried in a desiccator. The resulting 3.3 g (88%) of crude product is recrystallized thrice from boiling alcohol. Since the obtained product still contains by-products arising from decomposition, it is recrystallized twice again from dry acetonitrile. In this way 0.35 g (10%) of the title compound is obtained as a completely pure substance; m.p.: 208°–211° C., $[\alpha]_D = -27.4°$ (c=1%, in acetone).

Analysis: calculated for $C_{19}H_{19}NO_7$ (M=373.37): C: 61.12%, H: 5.13%, N: 3.71%; found: C: 60.65%, H: 5.11%, N: 3.73%.

IR (in KBr): 3360 (OH), 1740 (CO) cm$^{-1}$.

$^1$H NMR (CDCl$_3$, 100 MHz): $\delta=9.29$ (d), 8.81 (dd), 8.36 (dt) (3×1 H, pyridine-ArH); 7.35–7.58 (m) (6H, ArH and pyridine-ArH); 5.95 (d) (1H, H-1, $J_{1,2}=8$ Hz); 5.57 (s) (1H, H-7), 3.40–4.44 (m) (7H, skeletal protons) ppm.

EXAMPLE 10

12.3 g (0.1 mole) of nicotinic acid are added to 88 g of propylene glycol, and the mixture is heated to 150° to 160° C. 0.1 g of p-toluenesulfonic acid are added to the mixture, and esterification is conducted at elevated temperature until the acid number of the mixture, being initially 56, decreases to about one-half (i.e. to about 28). This requires about 12 to 36 hours of heating. Thereafter the mixture is cooled to room temperature.

Sodium hydroxide, equivalent to the acid number of the above mixture, is dissolved in water to obtain 50 g of an alkaline solution. When the acid number of the mixture is 28, 2 g (0.05 mole) of sodium hydroxide and 48 g of water are required. Glucosamine hydrochloride, equivalent to the sodium hydroxide content of the former solution, is dissolved in water to obtain 50 g of an aqueous solution. 5.39 g of glucosamine hydrochloride are equivalent to 1 g of sodium hydroxide; thus if the acid number of the above mixture is 28, 10.78 g (0.05 mole) of glucosamine hydrochloride and about 39.22 g of water are required.

The sodium hydroxide solution is added first to the stirred propylene glycol solution, previously cooled to room temperature, and thereafter the aqueous solution of glucosamine hydrochloride is introduced.

200 g of a solution are obtained. 100 g of the resulting solution contain some sodium chloride, 7.5 g (0.025 mole, 7.5%) of nicotinic acid salt of glucosamine, 4.5 g (0.025 mole, 4.5%) of propylene glycol mononicotinic acid ester (taken together, equivalent to 6 g, 0.05 mole, 6%, of nicotinic acid), furthermore water and the excess of propylene glycol as inert solvent.

EXAMPLE 11

Hair shampoo containing 2-deoxy-2-amino-glucose nicotinate (nicotinic acid salt of glucosamine)

22 parts by weight of (C$_{12-14}$ alkyl)-diglycolether sulfate sodium salt (a 30% solution), 22 parts by weight of fatty acid sarcoside sodium salt (a 30% solution), 2 parts by weight of a 2-deoxy-2-amino-glucose nicotinate solution prepared as described in Example 3. 0.5 part by weight of mannitol, 0.1 part by weight of polybromosalicylic anilide, 0.5 part by weight of polyvinyl pyrrolidone, 0.1 part by weight of concentrated chamomile solution and an appropriate odouring agent are admixed with each other, and the mixture is dissolved in water to obtain 100 parts by weight of a hair shampoo.

EXAMPLE 12

Alcoholic liniment for stimulating scalp and hair bulbs 1 part by weight of a glucose mononicotinic acid ester solution prepared as described in Example 1 and 1 part of a propylene glycol mononicotinic acid ester solution prepared as described in Example 6 are added to 50 parts by weight of isopropanol. Thereafter an odouring substance, 0.5 part by weight of sorbitol and concentrated aqueous chamomile solution are introduced to obtain 100 parts by weight of a liniment.

EXAMPLE 13

Liniment against rheumatism 10 parts by weight of a mannitol mononicotinic acid ester solution prepared as described in Example 2, 3 parts by weight of ethyl acetate and 0.5 part by weight of menthol are added to 55 parts by weight of 96% ethanol, and then a sufficient amount of water is introduced to obtain 100 parts by weight of a liniment.

EXAMPLE 14

Tooth paste against paradentosis 35 parts by weight of calcium dihydrophosphate, 10 parts by weight of a sorbitol mononicotinic acid ester solution prepared as described in Example 2, 5 parts by weight of sucrose, 2 parts by weight of sodium laurylsarcosinate and 1.5 parts by weight of Tylose are added to 15 parts by weight of glycerol, and then a sufficient amount (about 25 parts by weight) of water are introduced to obtain 100 parts by weight of a tooth paste.

EXAMPLE 15

5 g of chamomile are boiled in 50 g of water for 3 minutes. The extract is filtered, the weight of the filtrate is adjusted to 50 g with warm water, and then 10 g of affinate and 40 g of glucose are added. Thereafter 2% of a compound prepared by any of Examples 1 to 10 is added to the mixture. The resulting solution is maintained at 80° C. for 20 minutes and then filled into a flask. The flask is closed tightly.

EXAMPLE 16

2 g of birch leaves are boiled in 35 g of water for 5 minutes. The mixture is filtered off, the weight of the filtrate is adjusted to 35 g with warm water, and then 10 g of affinate, 25 g of glucose and 30 g of sucrose are dissolved in it. 5% of a compound prepared by any of Examples 1 to 10 is added to the mixture, the resulting solution is maintained at 85° C. for 15 minutes, then it is filled into a flask, and the flask is closed tightly.

EXAMPLE 17

3 g of chamomile are boiled in 40 g of water for 3 minutes. The mixture is filtered, and 10 g of affinate and 50 g of sucrose are added to the filtrate. The solids are dissolved under stirring. 1 g of biotin-D is admixed with 100 ml of water, one drop of an indicator is added to the mixture, and the pH of the mixture is adjusted to 7.5 with 0.1 n aqueous sodium hydroxide solution, whereupon biotin-D dissolves. The resulting solution is diluted with water to a final volume of 1000 ml. 1 ml of the diluted solution is added to the aqueous plant extract obtained as described above, and 8% of a compound prepared by any of Examples 1 to 10 is added to the resulting mixture. The obtained solution is maintained at 70° C. for 30 minutes, thereafter it is filled into a flask and the flask is closed tightly.

What we claim is:

1. A composition for topical application having vasodilator effect, containing 0.06 to 10% by weight, calculated on the total weight of the composition, of a reaction product of nicotinic acid, a nicotinic acid salt or a nicotinic acid halide and a polyol selected from the group consisting of glucose, mannitol, sorbitol, glucosamine hydrochloride, ethylene glycol, polyethylene glycol, dipropylene glycol, propylene glycol, arabite and 4,6-O-benzylidene-D-glycopyranose together with a diluent acceptable for topical application.

2. A composition as claimed in claim 1, containing also affinate.

3. A composition as claimed in claim 1, in which said product is d-glucose mononicotinic acid ester.

4. A composition as claimed in claim 1, in which said product is mononicotinic acid ester of mannitol or sorbitol.

5. A composition as claimed in claim 1, containing also a solution of 2-deoxy-2-amino-glucose nicotinate.

6. A composition as claimed in claim 1, in which said product is a nicotinic acid ester of ethylene glycol.

7. A composition as claimed in claim 1, in which said product is glucosamine nicotinate.

8. A composition as claimed in claim 1, in which said product is mononicotinic acid ester of polyethylene glycol.

9. A composition as claimed in claim 1, in which said product is mononicotinic acid ester of dipropylene glycol.

10. A composition as claimed in claim 1, in which said product is mononicotinic acid ester of propylene glycol.

11. A composition as claimed in claim 1, in which said product is mononicotinic acid ester of arabite.

* * * * *